United States Patent
Uzio et al.

(10) Patent No.: US 6,498,280 B1
(45) Date of Patent: Dec. 24, 2002

(54) CATALYST COMPRISING AN ELEMENT FROM GROUPS 8, 9 OR 10 WITH GOOD ACCESSIBILITY, AND ITS USE IN A PARAFFIN DEHYDROGENATION PROCESS

(75) Inventors: Denis Uzio, Marly le Roi (FR); Blaise Didillon, Rueil-Malmaison (FR); Emmanuel Pellier, Verriere (FR)

(73) Assignee: Institut Francais du Petrole (FR)

( * ) Notice: Subject to any disclaimer, the term of this patent is extended or adjusted under 35 U.S.C. 154(b) by 0 days.

(21) Appl. No.: 09/557,829

(22) Filed: Apr. 25, 2000

(30) Foreign Application Priority Data

Apr. 26, 1999 (FR) .............................. 99 05294

(51) Int. Cl.$^7$ .......................... C07C 5/333; C07C 5/23; C07C 5/25; B01J 23/40; B01J 23/42

(52) U.S. Cl. ........................ 585/654; 585/660; 585/661; 502/326; 502/327; 502/328; 502/330; 502/332; 502/333; 502/334; 502/335; 502/336; 502/337; 502/338; 502/339

(58) Field of Search ................................ 502/326, 327, 502/328, 330, 332, 333, 334, 335, 336, 337, 338, 339; 423/22, 89, 111, 138, 155, 179; 585/660, 661, 654

(56) References Cited

U.S. PATENT DOCUMENTS

| | | | | |
|---|---|---|---|---|
| 3,892,657 A | | 7/1975 | Wilhelm ..................... 208/139 |
| 3,951,868 A | * | 4/1976 | Wilhelm ............... 252/466 PT |
| 3,959,121 A | * | 5/1976 | Antos ........................ 208/139 |
| 3,960,710 A | * | 6/1976 | Pollitizer et al. ........... 208/139 |
| 4,020,012 A | * | 4/1977 | Miura et al. ................ 252/441 |
| 4,048,245 A | * | 9/1977 | Pollitizer et al. ....... 260/668 D |
| 4,048,246 A | * | 9/1977 | Antos ...................... 260/668 D |
| 4,110,200 A | * | 8/1978 | Antos ........................ 208/139 |
| 4,149,961 A | * | 4/1979 | Antos ........................ 208/139 |
| 4,179,359 A | * | 12/1979 | Hayes et al. ............... 208/139 |
| 4,179,405 A | * | 12/1979 | Antos ........................ 252/441 |
| 4,312,789 A | * | 1/1982 | Antos ........................ 252/441 |
| 4,430,517 A | * | 2/1984 | Imai et al. .................. 585/660 |
| 4,506,032 A | * | 3/1985 | Imai et al. .................. 502/223 |
| 4,522,935 A | * | 6/1985 | Robinson et al. ........... 502/223 |
| 4,542,248 A | * | 9/1985 | Lucien ....................... 585/322 |
| 4,551,574 A | * | 11/1985 | Imai et al. .................. 585/660 |
| 4,672,146 A | * | 6/1987 | Abrevaya et al. ........... 585/660 |
| 4,677,237 A | * | 6/1987 | Imai et al. .................. 585/444 |
| 4,762,960 A | * | 8/1988 | Imai ........................... 585/660 |
| 4,786,625 A | * | 11/1988 | Imai et al. .................. 502/326 |
| 4,827,072 A | * | 5/1989 | Imai et al. .................. 585/443 |
| 4,939,110 A | * | 7/1990 | Sachtler et al. .............. 502/66 |
| 4,964,975 A | * | 10/1990 | Chao et al. ................. 208/139 |
| 5,017,541 A | * | 5/1991 | Schmidt et al. ............. 502/169 |
| 5,128,300 A | * | 7/1992 | Chao et al. ................. 502/227 |
| 5,401,705 A | * | 3/1995 | Amelse ...................... 502/174 |
| H1447 H | * | 6/1995 | Linton ....................... 428/404 |
| 5,436,383 A | * | 7/1995 | Le Peltier et al. .......... 585/655 |
| 5,672,801 A | * | 9/1997 | Didillon et al. ............. 585/661 |
| 5,677,260 A | * | 10/1997 | Dongara et al. ............ 502/339 |
| 5,744,682 A | * | 4/1998 | McBride, Jr. et al. ....... 585/728 |
| 5,858,908 A | * | 1/1999 | Bogdan et al. .............. 502/227 |
| 5,866,746 A | * | 2/1999 | Didillon et al. ............. 585/661 |
| 5,883,039 A | * | 3/1999 | McBride, Jr. et al. ....... 502/327 |
| 6,013,173 A | * | 1/2000 | Bogdan ...................... 208/139 |
| 6,045,689 A | * | 4/2000 | Alario et al. ................ 208/139 |
| 6,197,721 B1 | * | 3/2001 | Didillon et al. ............. 502/326 |
| 6,218,334 B1 | * | 4/2001 | Alario et al. ................ 502/226 |
| 6,239,063 B1 | * | 5/2001 | Bogdan ...................... 502/325 |

FOREIGN PATENT DOCUMENTS

| EP | 0 714 872 A3 | 6/1996 |
| EP | 0 749 779 A1 | 12/1996 |

\* cited by examiner

*Primary Examiner*—Wayne A. Langel
*Assistant Examiner*—Cam N. Nguyen
(74) *Attorney, Agent, or Firm*—Millen, White, Zelano & Branigan, P.C.

(57) ABSTRACT

A catalyst comprising at least one support, at least one element from groups 8, 9 or 10 of the periodic table, at least one element from group 14 of the periodic table, at least one element from group 13 of the periodic table, at least one alkali or alkaline-earth metal, and, optionally, at least one halogen in an amount in the range from 0 to 0.2% by weight with respect to the total catalyst weight, the catalyst being characterized in that the accessibility of the element from groups 8, 9 or 10 is more than 50%. The invention also concerns a process for preparing a catalyst and the use of the catalyst in a process for dehydrogenating paraffins containing 3 to 22 carbon atoms per molecule.

22 Claims, No Drawings

CATALYST COMPRISING AN ELEMENT FROM GROUPS 8, 9 OR 10 WITH GOOD ACCESSIBILITY, AND ITS USE IN A PARAFFIN DEHYDROGENATION PROCESS

TECHNICAL FIELD

The invention relates to catalysts used in converting hydrocarbons and in particular to the paraffin dehydrogenation reaction. The invention pertains to a novel catalyst and to the preparation method carried out to synthesise it. The invention also relates to the use of said catalyst in paraffin dehydrogenation.

Alkenes constitute the feed of choice for the petrochemical industry. Steam cracking and catalytic cracking processes constitute the principle sources of alkenes. However, those two processes also produce by-products and the demand for specific alkenes which would be more expensive to produce by cracking is increasing.

For this reason, in some cases the direct production of alkenes remains an unavoidable step. This is the case with propylene, isobutene and long chain linear alkenes for producing polypropylene, MTBE and LAB (linear alkyl benzene) respectively.

The principal limitations of the dehydrogenation reaction are that the thermodynamic equilibrium limits the degree of conversion per pass and that the reaction is highly endothermic. These two features are determining factors in choosing process techniques and also in the design of the catalyst.

Thus n-paraffins containing 10 to 14 carbon atoms are generally dehydrogenated at temperatures of about 450–500° C. with a degree of conversion per pass in the range 10% to 25%, limited by the thermodynamics.

A high temperature operation is necessary to keep the degree of conversion close to the thermodynamic equilibrium, but a high temperature also encourages a certain number of side reactions, leading to a poor quality product. Such reactions include those leading to the formation of light products (cracking, hydrogenolysis), highly unsaturated compounds precursors of carbonaceous deposits, i.e., deactivation initiators (dehydrocyclisation, deep dehydrogenation) such as aromatic compounds or diolefins, and skeletal isomerisation reactions responsible for the formation of branched molecules. Because of such secondary reactions, under these particularly severe operating conditions it is very difficult to keep the activity high over long periods.

PRIOR ART

Means for limiting such secondary reactions can be aimed at the process and/or the catalytic formulation. Thus European patent EP-B1-0 462 094 claims adding hydrogen to the feed in $H_2$/hydrocarbon mole ratios in the range 0.5 to 1.9. The purpose of adding hydrogen is to limit or retard the formation of coke on the catalyst surface without observing a negative effect on n-paraffin conversion.

A further solution proposed in U.S. Pat. Nos. 3,448,165, 3,907,921 and 5,233,118 consists of injecting a small quantity of water and/or sulphur with the hydrocarbon feed to be dehydrogenated. The water can be injected at a rate which is constant or which gradually increases with the catalyst function time. It was reported that an optimum as regards performance was obtained by increasing the injection of water with the temperature of the reactor during the operating cycle.

The other route which has been explored, again to improve the catalytic system performance, in particular stability, consists of determining the optimum physicochemical properties. Thus U.S. Pat. No. 4,716,143 uses a catalyst based on a supported platinum such that the platinum distribution is limited to the external surface of the support over a maximum thickness of 400 $\mu$m. The advantage of such a choice resides in the fact that distribution at the periphery of the support can limit side reactions and as a result can improve catalyst performance. However, that type of distribution can only rarely produce platinum/modifier atomic ratios which are homogeneous on the particle scale (nanometers). Further, an excess concentration of active phase on the surface can cause diffusional limitations on the catalyst grain level (extragranular diffusion) and thus reduce the overall yield of the reaction.

The most frequently used platinum modifiers include elements from groups 14 and 13 and in particular tin (U.S. Pat. No. 3,745,112). The role of the tin present on the surface of the catalyst in the oxidation state +2, or more preferably +4, is to minimise the isomerisation and cracking reactions which occur at the acid sites of the support. A further example of a platinum modifier is indium, cited in particular in U.S. Pat. No. 4,551,574, European patent EP-B-0 183 861 and Japanese patent JP-B-91041211. Indium improves stability by also inhibiting secondary deep dehydrogenation reactions (polyolefins) and skeletal isomerisation reactions (branched hydrocarbons). It should be noted that the promoting power of such elements as regards platinum is also well known within the well-studied context of catalytic cracking catalysts.

As regards platinum based catalysts, because of the high cost of platinum, there is an interest in dispersing the metallic phase to the best extent, i.e., in increasing the proportion of noble metal in contact with the surface and the molecules to be transformed. It is important to develop a maximum specific metal surface area (surface area expressed per gram of metal) to obtain as high a degree of conversion as possible. Thus a drop in accessibility equivalent to an increase in particle size or a rearrangement of elementary particles is highly prejudicial to the productivity of the reaction. Thus one aims to minimise the particle size during preparation and to maintain this dispersion high, but thermodynamically unstable. The presence of a sufficient quantity of chlorine can constitute an answer to this problem. Chlorine is known to have a stabilising and even a re-dispersing effect on very small platinum particles. U.S. Pat. No. 4,430,517 cites an example of a chlorine content of more than 2.5% by weight for a platinum content of 0.75% by weight, corresponding to a Cl/Pt atomic ratio of about 19. That stabilising effect has also been known for a long time for catalytic reforming catalysts (U.S. Pat. Nos. 2,479,109, 2,602,772). However, while in the latter case, cyclisation and skeletal isomerisation reactions are highly desirable, in the case of dehydrogenation in general and dehydrogenation of paraffins containing 6 to 22 carbon atoms in particular, these reactions constitute side reactions which should be limited to avoid rapid deactivation of the catalyst. Thus adding chlorine causes a problem as a result of the secondary reactions which it encourages.

In order to limit secondary reactions, depositing an alkali or alkaline-earth, the role of which consists of contributing to neutralisation of the acid sites of the support with a weak and medium force, is important. Even a limited addition of lithium (0.1% by weight) can neutralise these acid sites which are responsible for the formation of isomerised and light products (cracking reactions). Aromatic compound formation is also reduced by adding lithium. However, this addition is also known to entrain a reduction in the total activity of the catalyst. This reduction is often linked to a phenomenon of coating the metallic phase with the alkali metal.

Conventional preparation methods cannot deposit sufficient amounts of alkali, in particular lithium, without producing a large drop in the accessibility of the platinum in the presence of a small quantity of a halogen. Studies in the literature have demonstrated this phenomenon when impregnating lithium into platinum based catalysts (Passos, Schmal, Frety, Catalysis Letters 14 (1994) 57–64).

To overcome this phenomenon, one route proposed in U.S. Pat. No. 5,536,695 consists of depositing lithium on an alumina support and carrying out a high temperature heat treatment to form a surface aluminate phase ($LiAl_5O_8$ or $LiAlO_2$). Platinum can then be deposited at the end of this step using a precursor, preferably an organic precursor. The use of an acid solution of a mineral precursor (hexachloroplatinic acid or hexahydroxyplatinic acid) suffers from the disadvantage of partially dissolving the aluminate support formed and thus leading to a loss of alkali metal. Further, inverting the aluminate formation and platinum deposition steps cannot be envisaged, since the heat treatment necessary for forming the aluminate phase, carried out at about 800° C., causes very substantial sintering of the platinum by particle aggregation. Further, the use of organic solutions is of low industrial importance because of the environmental problems and safety concerns linked thereto.

Finally, the support can also play a substantial role in the stability of the catalytic system as taught by patents U.S. Pat. Nos. 4,672,146 and 358,920. The pore size and void fraction parameters developed by pores over 60 or 100 nm in size (macropores) determine the final transport properties especially in the case of sterically hindered hydrocarbon molecules (long chains, for example).

SUMMARY OF THE INVENTION

The invention provides a catalyst comprising a support, at least one element from groups 8, 9 or 10 of the periodic table ("Handbook of Physics and Chemistry", 76th edition), at least one element from group 14 of the periodic table, at least one element from group 13 of the periodic table, at least one alkali or alkaline-earth metal from the periodic table, and optionally at least one halogen in an amount in the range 0 to 0.2% by weight with respect to the total catalyst weight, said catalyst being characterized in that the accessibility of the element from groups 8, 9 or 10 is more than 50%. The invention also concerns a process for preparing a catalyst and the use of the catalyst in a process for dehydrogenating paraffins containing 3 to 22 carbon atoms per molecule, The term "accessibility" as used in the present invention means the quantity of the element from groups 8, 9 or 10 accessible to the feed to be converted with respect to the total quantity of the element from groups 8, 9 or 10 present on the catalyst.

IMPORTANCE OF THE INVENTION

The invention enables a novel supported catalyst to be prepared which contains both an alkali or alkaline-earth metal in an amount of more than 500 ppm and particles of metals from groups 8, 9 or 10 with an accessibility of more than 50% while keeping the chlorine content to below 0.2% by weight. It has been discovered that the fact that it contains little chlorine, a stabilizing agent for small platinum particles, for the type of support under consideration, does not result in an accelerated aging of the catalyst by sintering but can substantially reduce the secondary reactions cited above. Finally, it has also been discovered that this catalyst can undergo a regenerative treatment by coke combustion without altering catalytic performance.

DESCRIPTION

The catalyst of the invention comprises a support, at least one element from groups 8, 9 or 10, at least one additional element selected from group 14 elements, at least one additional element selected from group 13 elements, at least one alkali or alkaline-earth and optionally at least one halogen in a maximum amount of 0.2% by weight with respect to the total catalyst weight.

The metal from groups 8, 9 or 10 is selected from platinum, palladium, rhodium, ruthenium, osmium, iridium, iron, cobalt and nickel, preferably selected from noble metals from groups 8, 9 or 10 and preferably platinum, where the content is in the range 0.01% to 5% by weight with respect to the total catalyst weight, preferably in the range 0.05% to 1%.

The group 14 metal is selected from tin, germanium and lead, preferably tin, in an amount in the range 0.01% to 5% by weight with respect to the total catalyst weight, and more preferably in the range 0.1% to 1%.

The group 13 metal is selected from indium, gallium and thallium, preferably indium, in an amount in the range 0.005% to 3% by weight with respect to the total catalyst weight, and more preferably in the range 0.01% to 1%.

The alkali metal is selected from lithium, sodium, potassium and caesium, preferably potassium, in an amount in the range 0.05% to 3% by weight with respect to the total catalyst weight, more preferably in the range 0.1% to 1%. If the catalyst contains it, the halogen is preferably chlorine in an amount in the range 0 to 0.2% by weight, preferably in the range 0 to 0.15%.

The invention is characterized in that the accessibility of the group VIII metal is more than 50%, preferably more than 60% and still more preferably more than 70%. The accessibility of the group VIII metal is measured by $H_2/O_2$ titration.

The catalyst supports of the invention are generally porous solids selected from refractory oxides, such as aluminas, silicas, magnesia, titanium oxide and zinc oxide. These last two oxides can be used alone or mixed with alumina. Further, the supports are preferably transition aluminas or silicas with a specific surface area in the range 25 to 300 $m^2/g$, preferably in the range 80 to 200 $m^2/g$. Natural compounds such as kieselguhr or kaolin can also be suitable as supports for the catalysts of the invention.

Preparation of the catalyst of the invention comprises, for example, successive steps for depositing, using any technique known to the skilled person, a group 13 metal, then a step for depositing a group 14 metal and a step for depositing a metal from groups 8, 9 or 10. These deposition steps can be carried out in any order. The metals are deposited such that the accessibility of the metal from groups 8, 9 or 10 is more than 50%. The metals can be deposited by dry impregnation or excess impregnation or by an ion exchange method. Calcining can be carried out by passing a stream of air at a temperature of about 500° C. with the aim of decomposing precursors and forming the metallic phases, and the desired interactions.

In accordance with the invention, the alkali or alkaline-earth metal is deposited by bringing the support into contact with at least one solution containing at least one precursor of at least one alkali or alkaline-earth metal. Deposition of the alkali or alkaline-earth metal is characterized in that the pH of the solution comprising the alkali or alkaline-earth metal precursor is less than 2. The solution comprising the alkali metal can also contain at least one metal from groups 8, 9 or 10 and/or at least one metal from group 14, and/or at least one group 13 metal. The pH of the solution comprising the alkali metal can be brought to a value of 2 or less using any method known to the skilled person. As an example, an acid selected from nitric acid, hydrochloric acid, sulphuric acid or hydrofluoric acid can be added. The pH is preferably adjusted by adding nitric acid.

A final heat treatment is aimed at decomposing the alkali metal precursor and eliminating the major portion of the halogen injected during the preceding operations. This step will be carried out, for example, by exposing the catalyst to a 1/1 molar air/water mixture at a temperature of about 500° C. for a period of 2 to 4 hours. This dehalogenation operation can optionally be carried out after depositing metals from groups 14 and 13 and from groups 8, 9 or 10. In the latter case, a heat treatment in dry air of the same type as above completes preparation of the catalyst.

Any other preparation method which is known to the skilled person may also be suitable, provided that the accessibility of the metal from groups 8, 9 or 10 is more than 50%.

The metal from groups 8, 9 or 10 can be introduced using any precursor which is known to the skilled person, such as halogenated salts and organometallic compounds. Preferably, a precursor of a metal from groups 8, 9 or 10 which is soluble in an aqueous medium, such as chloroplatinic acid, is used.

The alkali metal, the group 14 metal and the group 13 metal can be introduced using any known precursor. As an example, decomposable salts can be used in the form of chlorides, bromides, nitrates, carbonates or acetates. It is also possible to use organometallic salts of metals from groups 14 and 13 such as tetrabutyltin or triphenylindium.

In one particular implementation of the invention, the precursor of the group 14 and/or precursor of the group 13 metal can be an organometallic compound with a carbon-group 14 or 13 metal bond, which is soluble in an aqueous medium. As an example, a tin complex from the alkyl allyl family can be used.

The invention also concerns the use of the catalyst in a hydrocarbon conversion process. As an example, the catalyst can be used to dehydrogenate paraffin feeds containing 3 to 22 carbon atoms, preferably 5 to 20 carbon atoms per molecule. This reaction is generally carried out at an operating pressure in the range 0.02 to 2 MPa, preferably in the range 0.05 to 0.5 MPa and at a temperature in the range 300° C. to 800° C., preferably in the range 400° C. to 550° C. The hydrogen/hydrocarbon mole ratio is generally in the range 0 to 20 and is preferably in the range 0 to 10. The hourly space velocity (expressed in liters of hydrocarbon per liter of catalyst per hour) is generally in the range 10 to 100 h$^{-1}$. The operating conditions can be adjusted within a wide range, depending on the nature of the treated feeds and the catalytic performances aimed at by the user in particular as regards olefin yield.

EXAMPLE 1
(In Accordance with the Invention)

A dehydrogenation catalyst A was prepared, containing 0.30% by weight of platinum, 0.33% by weight of tin, 0.11% by weight of indium, 0.35% by weight of lithium and 0.08% by weight of chlorine deposited on a delta alumina with a specific surface area of 130 m$^2$/g.

The support (200 g) was brought into contact with 900 ml of distilled water by maintaining the temperature of the bed constant. 0.8 g of tin in the form of SnCl$_2$ was gradually added in the presence of HCl After 4 h of contact, the catalyst was then dried. Next, the catalyst was brought into contact with 650 ml of distilled water to which 50 ml of an aqueous solution containing 0.51 g of indium in the form of In(NO$_3$)$_3$ had been added. After 3 h of contact, the catalyst was dried. Finally, the platinum was deposited by again bringing the catalyst into contact with 650 ml of distilled water to which 0.6 g of Pt had been added in the form of H$_2$PtCl$_6$. After 3 h of impregnation, the catalyst was filtered, and dried at 150° C. for 2 h in a flow of 200 l/h of air with a temperature rise of 5° C./min. After this stage, the catalyst was calcined at 530° C. for 2 hours in a flow rate of 200 l/h of air with a temperature rise of 5° C./min.

The final lithium impregnation was carried out by adding 0.7 g of lithium in the form of LiNO$_3$ dissolved in 205 ml of distilled water where the pH had been adjusted to 1.3 by adding 66% by weight nitric acid. The catalyst was dried at 150° C. for 2 h in a flow of 200 l/h of air with a temperature rise of 5° C./min then calcined at 550° C. for 4 h in an air/water mixture (50/50 molar) at an HSV of 100 h$^{-1}$ and with a temperature rise of 5° C./min. After stopping the water injection, the catalyst was calcined at 550° C. for 1 h. The elements were all homogeneously distributed in the support beads.

The accessibility of the platinum, measured by H$_2$/O$_2$ titration using the method described below, was 70%.

H$_2$/O$_2$ titration consists of measuring the volume of oxygen consumed by reaction (1) after a catalyst reduction step:

$$Pt_S\text{—}H+\tfrac{3}{4}O_2 \rightarrow Pt_S\text{—}O+\tfrac{1}{2}H_2O \qquad (1)$$

Where Pt$_S$ designates the superficial platinum atoms.

The catalyst is then reduced in hydrogen at 450° C. then, after bringing back to ambient temperature in hydrogen, known volumes of oxygen are injected. The oxygen consumption is monitored by chromatography, and signal integration enables the volume of oxygen consumed by reaction (1) to be deduced by difference from the total volume injected. Using the stoichiometric coefficients of reaction (1), the fraction of platinum on the surface, or accessibility, can be determined by the relationship:

$$D = \frac{4 V O_2 M_{Pt}}{3 V_M [\% Pt / 100]}$$

where:

M$_{Pt}$=molar mass of platinum (195.09 g.mol$^{-1}$);

V$_M$=molar volume of gas (24400 ml/mol) at 25° C.;

VO$_2$=volume measured corresponding to the oxygen consumption;

% Pt=weight of platinum in the catalyst.

EXAMPLE 2
(In Accordance with the Invention)

A dehydrogenation catalyst B was prepared, containing 0.30% by weight of platinum, 0.33% by weight of tin, 0.11% by weight of indium, 0.60% by weight of lithium and 0.09% by weight of chlorine. The elements In, Sn and Pt are deposited using the same protocol as that described for Example 1. Lithium was deposited by contact with an aqueous lithium nitrate solution containing 1.2 g of Li in the form of LiNO$_3$ with a pH of 1.3.

All of the elements were homogeneously distributed in the support beads. The platinum accessibility, measured by H$_2$/O$_2$ titration, was 60%.

EXAMPLE 3
(In Accordance with the Invention)

A catalyst C was prepared containing 0.31% by weight of platinum, 0.32% by weight of tin, 0.13% by weight of indium, 0.35% by weight of lithium and 0.09% by weight of chlorine. The catalyst was prepared using the conditions described in Example 1, by introducing tin which was produced under the following conditions: 120 ml of water at a pH of 4 containing trimethyl tin chloride was brought into contact with the support. After drying and calcining at 450° C., the other elements were introduced using the methods described in Example 1.

All of the elements were homogeneously distributed in the support beads. The platinum accessibility, measured by H$_2$/O$_2$ titration, was 73%.

EXAMPLE 4
(In Accordance with the Invention: Regenerated Catalyst B)

Catalyst B of Example 2 was regenerated, becoming catalyst D, comprising heat treatment in a high temperature air/nitrogen flow of variable concentration to 350° C. (temperature rise 5° C./min) monitoring the quantity of heat released (T reference−T catalyst<2° C.). After this treatment, the accessibility determined by H$_2$/O$_2$ titration was 55%.

EXAMPLE 5

Comparative

A dehydrogenation catalyst E was prepared containing 0.31% by weight of platinum, 0.34% by weight of tin, 0.14% by weight of indium, 0.65% by weight of lithium and 0.12% by weight of chlorine. The elements In, Sn and Pt were deposited using the same protocol as in Example 1. The lithium was deposited by contact with an aqueous lithium nitrate solution with no re-acidification with HNO$_3$.

All of the elements were homogeneously distributed in the support beads. The platinum accessibility, measured by H$_2$/O$_2$ titration, was 20%.

EXAMPLE 6

Comparative

A dehydrogenation catalyst F was prepared containing 0.31% by weight of platinum, 0.35% by weight of tin, 0.14% by weight of indium, 0.65% by weight of lithium and 0.57% by weight of chlorine. The preparation used the protocol presented in Example 1. Only the precursor (and the quantity used) of lithium was modified, being a lithium chloride instead of a nitrate. The platinum particle accessibility was 63%.

EXAMPLE 7

Comparative

A dehydrogenation catalyst G containing 0.31% by weight of platinum, 0.36% by weight of tin, 0.6% by weight of lithium, 0.15% by weight of indium and 0.12% by weight of chlorine was prepared using techniques known to the skilled person with formation of a lithium aluminate.

156 ml of an aqueous lithium acetate solution containing 0.9 g of lithium was added to 150 g of an alumina support. The system was left in contact with the alumina for 3 hours, then dried for 1 hour at 120° C. and calcined for 2 hours at 750° C. at an HSV (volume of air per kilogram of catalyst per hour) of 2000 h$^{-1}$. The tin, indium and platinum were deposited in successive dry impregnation steps (bringing the alumina into contact with a volume of solution corresponding to the pore volume of the alumina) with intermediate drying heat treatments of 1 hour at 120° C. and a final calcining heat treatment of 2 hours at 530° C. X ray diffraction analysis showed the presence of lithium aluminate at d=2.38$_E$-10 m, d=1.4$_E$-10 m, d=1.98$_E$-10 m and d=2.8$_E$-10 m in the presence of unmodified alumina. The accessibility of catalyst G, determined by H$_2$/O$_2$ titration, was 42%.

EXAMPLE 8
(Comparison of Catalytic Performances)

Catalysts A to G underwent a test for dehydrogenating an n-paraffin feed with a number of carbon atoms in the range 10 to 14. The reaction was carried out isothermally at 450° C., P=2.4 bars absolute; the hydrocarbon feed flow rate was 200 ml/h and that of hydrogen was 127 l/h, corresponding to a H$_2$/hydrocarbon mole ratio of 6 and an HSV of 20 h$^{-1}$. Water addition was maintained at 2000 ppm throughout the test. The mass of the catalyst used was 4.5 g. The catalyst was first calcined in an air flow of 15 l/h for 2 h at 500° C. with a temperature rise of 50° C./h. After allowing it to cool to ambient temperature and purging under nitrogen, the catalyst was placed under a pure hydrogen stream (10 l/h) at 430° C. for 4 h with a temperature rise of 50° C./h. Finally, the temperature was brought to 450° C. with an injection of paraffin feed and of water.

The reaction products were analysed by gas chromatography (50 m PONA column, internal diameter 0.2 mm, OV1 phase) using the following procedure: temperature rise from 40° C. to 200° C. (2°/min), then rise to 280° C. (10°/min), constant for one minute at 280° C. The leak rate was 200 ml/min and the volume of the injection loop was 0.5 μl. The temperature of the flame ionisation detector (FID) and of the injector was 280° C.

|  | A | B | C | D | E | F | G |
|---|---|---|---|---|---|---|---|
| n-paraffin conversion C10–C14* (%) | 8.2 | 7.5 | 8.2 | 7.6 | 2.1 | 7.8 | 5.6 |
| Olefin yield C10–C14 (%) | 7.7 | 7.0 | 7.8 | 7.3 | 2 | 6.9 | 5.4 |
| Aromatics yield C10–C14 (%) | 0.22 | 0.12 | 0.21 | 0.18 | 0.05 | 0.35 | 0.09 |
| Diolefins yield C10–C14 (%) | 0.13 | 0.22 | 0.13 | 0.08 | 0.02 | 0.24 | 0.07 |

-continued

|  | A | B | C | D | E | F | G |
|---|---|---|---|---|---|---|---|
| Iso-paraffin yield C10–C14 (%) | 0.10 | 0.09 | 0.10 | 0.04 | 0.03 | 0.16 | 0.04 |
| Yield of other products C10⁻ and C14⁺ⁿ (%) | 0.05 | 0.07 | 0 | 0 | 0 | 0.15 | 0 |
| Deactivation slope** (%/h) | 0.0052 | 0.0033 | 0.0051 | 0.0028 | 0.0025 | 0.0045 | 0.0015 |
| Accessibility*** (%) | 70 | 60 | 73 | 55 | 20 | 63 | 42 |

*: Determined after 100 h of operation.
**: Defined as the slope of the graph of the C10–C14 n-paraffin conversion against time.
***: Determined by $H_2/O_2$ titration.

The results of the above table show that the activity of the catalysts of the invention is at least as good as that of the prior art catalysts and especially that the selectivity for the desired products (olefins) surprisingly increases for the catalysts of the present invention due to a reduction in losses by aromatisation and dehydrogenation to diolefins (catalysts A, B, C and D compared with catalyst F).

What is claimed is:

1. A catalyst comprising at least one support, at least one element from groups 8, 9 or 10 of the periodic table, at least one element from group 14 of the periodic table, at least one element from group 13 of the periodic table; at least one alkali or alkaline-earth metal, and optionally, at least one halogen in an amount of less than or equal to 0.2% by weight, with respect to the total catalyst weight, said catalyst being prepared according to a process comprising introducing the alkali or alkaline-earth metal onto the support by bringing the support into contact with at least one acid solution comprising at least one precursor or at least one alkali or alkaline-earth metal and devoid of any element from groups 8, 9, 10, 13 and 14, wherein the pH of the acid solution is less then 2 and adjusted by addition of $HNO_3$ so that the accessibility of the element from groups 8, 9 or 10 is more than 50%, as measured by $H_2/O_2$ titration.

2. A catalyst according to claim 1, wherein the accessibility of the element from groups 8, 9 or 10 is more than 60%.

3. A catalyst according to claim 1, wherein the accessibility of the element from groups 8, 9 or 10 is more than 70%.

4. A catalyst according to claim 1, comprising, by weight with respect to the total catalyst weight, 0.01% to 5% of at least one element from groups 8, 9 or 10, 0.01% to 5% of at least one element from group 14, 0.005% to 3% of at least one element from group 13 and 0.05% to 3% by weight of at least one alkali or alkaline-earth metal.

5. A catalyst according to claim 4, wherein the support is a refractory oxide with a specific surface area in the range of 25 to 300 $m^2/g$.

6. A catalyst according to claim 5, wherein the oxide support is alumina.

7. A catalyst according to claim 1, comprising less then 0.15% by weight of halogen with respect to the total catalyst weight.

8. A catalyst according to claim 1, comprising at least 0.1% by weight of alkali or alkaline-earth metal with respect to the total catalyst weight.

9. A catalyst according to claim 1, wherein the element from groups 8, 9 or 10 is platinum.

10. A catalyst according to claim 1, wherein the element from group 14 is tin.

11. A catalyst according to claim 1, wherein the element from group 13 is indium.

12. A catalyst according to claim 1, wherein the catalyst hydroconverts hydrocarbons under hydroconverting conditions with a selectivity for $C_{10}$–$C_{14}$ olefin of at least 93.4%.

13. A catalyst according to claim 12, wherein the acidic solution with a pH of 1.3 comprises nitric acid and water, and the at least one alkali or alkaline-earth metal is Li.

14. A catalyst according to claim 1, wherein the catalyst hydroconverts hydrocarbons under hydroconverting conditions with a selectivity of aromatics of no more then 2.7%.

15. A catalyst according to claim 14, wherein the acidic solution with a pH of 1.3 comprises nitric acid and water, and the at least one alkali or alkaline-earth metal is Li.

16. A catalyst according to claim 1, wherein the acidic solution with a pH of 1.3 comprises nitric acid and water, and the at least one alkali or alkaline-earth metal is Li.

17. A catalyst according to claim 1, wherein the group 14 metal, the group 13 metal, and the metal from groups 8, 9 or 10 are introduced onto the support in any order.

18. A catalyst according to claim 1, wherein the group 14 metal and/or the group 13 metal are introduced in the form of an organometallic compound comprising a carbon-metal bond, said organometallic compound being soluble in aqueous solvents.

19. A catalyst according to claim 1, further comprising subjecting the catalyst to a catalyst dehalogenation step.

20. In a process comprising catalytically hydroconverting hydrocarbons under hydroconverting conditions, the improvement comprising employing a catalyst according to claim 1.

21. A process according to claim 20, for dehydrogenating paraffins containing 3 to 22 carbon atoms per molecule.

22. A process according to claim 20, for dehydrogenating paraffins containing 5 to 20 carbon atoms per molecule.

* * * * *